(12) United States Patent
Castagna et al.

(10) Patent No.: US 11,457,843 B2
(45) Date of Patent: Oct. 4, 2022

(54) SYSTEMS AND METHODS FOR COMMUNICATION WITH ANALYTE SENSOR ELECTRONICS

(71) Applicant: DexCom, Inc., San Diego, CA (US)

(72) Inventors: Patrick John Castagna, San Diego, CA (US); David A. Keller, Encinitas, CA (US); Warren Terry, Poway, CA (US)

(73) Assignee: Dexcom, Inc., San Diego, CA (US)

( * ) Notice: Subject to any disclaimer, the term of this patent is extended or adjusted under 35 U.S.C. 154(b) by 61 days.

(21) Appl. No.: 16/522,508

(22) Filed: Jul. 25, 2019

(65) Prior Publication Data

US 2020/0037939 A1    Feb. 6, 2020

Related U.S. Application Data

(60) Provisional application No. 62/714,485, filed on Aug. 3, 2018.

(51) Int. Cl.
*A61B 5/00* (2006.01)
*A61B 5/145* (2006.01)
*H04W 76/14* (2018.01)
*H04L 67/12* (2022.01)

(52) U.S. Cl.
CPC ........ *A61B 5/14546* (2013.01); *A61B 5/0004* (2013.01); *A61B 5/14532* (2013.01); *H04L 67/12* (2013.01); *H04W 76/14* (2018.02)

(58) Field of Classification Search
CPC ............ A61B 5/14546; A61B 5/14532; A61B 5/0002; A61B 5/6833; H04W 76/14
See application file for complete search history.

(56) References Cited

U.S. PATENT DOCUMENTS

| | | |
|---|---|---|
| 6,001,067 A | 12/1999 | Shults et al. |
| 6,424,847 B1 | 7/2002 | Mastrototaro et al. |
| 6,477,395 B2 | 11/2002 | Schulman et al. |
| 6,512,939 B1 | 1/2003 | Colvin et al. |
| 6,565,509 B1 | 5/2003 | Say et al. |
| 6,579,690 B1 | 6/2003 | Bonnecaze et al. |
| 6,931,327 B2 | 8/2005 | Goode, Jr. et al. |
| 7,310,544 B2 | 12/2007 | Brister et al. |
| 10,765,353 B2 * | 9/2020 | Biederman .......... A61B 5/6801 |
| 2005/0027463 A1 | 2/2005 | Goode, Jr. et al. |
| 2005/0043598 A1 | 2/2005 | Goode, Jr. et al. |

(Continued)

*Primary Examiner* — Christian Jang
(74) *Attorney, Agent, or Firm* — Patterson + Sheridan, LLP

(57) ABSTRACT

Systems and methods for wireless communication of analyte information are disclosed. Example embodiments include an analyte sensor system. The analyte sensor system may include an analyte sensor to gather information related to a level of an analyte in a host. The analyte sensor system may include circuitry to transmit and receive wireless signals using a first antenna. The analyte sensor may be coupled to the circuitry before the analyte sensor system is transitioned into an operational state. The analyte sensor system may include a second antenna to receive an input signal from a source external to the analyte sensor system and to transmit a modified signal. The circuitry may use the first antenna to receive the modified signal. The analyte sensor system may transition into the operational state in response to the modified signal received using the first antenna.

11 Claims, 8 Drawing Sheets

(56) References Cited

U.S. PATENT DOCUMENTS

| | | |
|---|---|---|
| 2005/0154271 A1 | 7/2005 | Rasdal et al. |
| 2005/0203360 A1 | 9/2005 | Brauker et al. |
| 2006/0020187 A1 | 1/2006 | Brister et al. |
| 2006/0222566 A1 | 10/2006 | Brauker et al. |
| 2006/0258929 A1 | 11/2006 | Goode, Jr. et al. |
| 2007/0016381 A1 | 1/2007 | Kamath et al. |
| 2007/0027385 A1 | 2/2007 | Brister et al. |
| 2007/0032706 A1 | 2/2007 | Kamath et al. |
| 2007/0197890 A1 | 8/2007 | Boock et al. |
| 2007/0203966 A1 | 8/2007 | Brauker et al. |
| 2007/0208245 A1 | 9/2007 | Brauker et al. |
| 2008/0033254 A1 | 2/2008 | Kamath et al. |
| 2008/0108942 A1 | 5/2008 | Brister et al. |
| 2008/0119703 A1 | 5/2008 | Brister et al. |
| 2009/0318792 A1 | 12/2009 | Fennell et al. |
| 2013/0137946 A1 | 5/2013 | Geske et al. |
| 2014/0247152 A1* | 9/2014 | Proud .................... G08C 17/02 340/870.07 |
| 2014/0266776 A1* | 9/2014 | Miller .................. A61B 5/6849 340/870.01 |
| 2017/0074757 A1* | 3/2017 | Garcia ................. A61B 5/0031 |
| 2017/0189614 A1* | 7/2017 | Mazlish ............. A61M 5/1452 |
| 2018/0182491 A1 | 6/2018 | Belliveau et al. |
| 2019/0159704 A1* | 5/2019 | Matikyan ........... A61B 5/14532 |
| 2019/0386711 A1* | 12/2019 | He ........................ H01Q 1/273 |

* cited by examiner

SYSTEMS AND METHODS FOR COMMUNICATION WITH ANALYTE SENSOR ELECTRONICS

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Application No. 62/714,485, filed Aug. 3, 2018. The aforementioned application is incorporated by reference herein in its entirety, and is hereby expressly made a part of this specification.

FIELD

Systems and methods for wireless communication of analyte information are disclosed. Example embodiments include an analyte sensor system. The analyte sensor system may include an analyte sensor to gather information related to a level of an analyte in a host. The analyte sensor system may include circuitry to transmit and receive wireless signals using a first antenna. The analyte sensor may be coupled to the circuitry before the analyte sensor system is transitioned into an operational state. The analyte sensor system may include a second antenna to receive an input signal from a source external to the analyte sensor system and to transmit a modified signal. The circuitry may use the first antenna to receive the modified signal. The analyte sensor system may transition into the operational state in response to the modified signal received using the first antenna.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which may require uncomfortable finger pricking methods. Due to the lack of comfort and convenience, a diabetic will normally only measure his or her glucose level two to four times per day. Unfortunately, these time intervals are spread so far apart that the diabetic will likely be alerted to a hyperglycemic or hypoglycemic condition too late, sometimes incurring dangerous side effects as a result. In fact, it is not only unlikely that a diabetic person will take a timely SMBG value, but will not know if the person's blood glucose value is going up (higher) or down (lower), due to limitations of conventional methods.

Consequently, a variety of non-invasive, transdermal (e.g., transcutaneous) and/or implantable electrochemical sensors are being developed for continuously detecting and/or quantifying blood glucose values. These sensors and associated devices are generally used to transmit raw or minimally processed data for subsequent analysis at a remote device, which can include a display. The transmission to and communication with wireless display devices can be wireless. The remote device can then be used to provide the user with information about the user's blood glucose levels. Because systems using such implantable sensors can provide more up to date information to users, they may reduce the risk of a user failing to regulate the user's blood glucose levels. Nevertheless, such systems typically still rely on the user to take action in order to regulate the user's blood glucose levels, for example, by making an injection. For example, such systems may typically include a glucose sensor implantable into a host and sensor electronics circuitry for processing and communicating glucose related information. In such systems, however, the sensor and the sensor electronics circuitry are usually designed to be connected for the first time by a user or host after the sensor has been implanted into the user. Accordingly, in view of such systems, there exists potential to reduce the amount of user interaction involved with deploying an analyte sensor system.

SUMMARY

In view of the above characteristics associated with some systems, there exists a need for an analyte sensor system in which an analyte sensor and analyte sensor electronics circuitry are configured to be electrically and mechanically coupled to each other before the analyte sensor is implanted into the user or host. The present disclosure relates generally to signaling exchanged with sensor electronics in connection with the wireless communication of analyte data gathered using an analyte sensor system. Such signaling may include, for example, signaling for controlling activation or operation of the analyte sensor system, signaling relating to pairing the analyte sensor system with remote device(s), and/or signaling relating to the communication and/or generation of analyte information. More particularly, certain embodiments of the present disclosure are directed to systems, methods, apparatuses, devices, etc. that facilitate such signaling with an analyte sensor system in which the analyte sensor is connected both electrically and mechanically to analyte sensor electronics circuitry before the analyte sensor is implanted in the host.

One example technique that may be used for detecting and/or controlling activation or triggering for the analyte sensor electronics circuitry in accordance with embodiments of the present disclosure can involve the exchange of wireless signaling. In embodiments, an external source (e.g., a display device or other component external to the analyte sensor system) may be used to send a wireless input signal to the analyte sensor system. The analyte sensor system can receive the wireless input signal using an antenna associated with the analyte sensor system, and can further use the received wireless input signal for purposes of activation/triggering, as described herein. The analyte sensor system may in certain cases use a wireless input signal for purposes of pairing and/or exchanging analyte information, as described herein.

Embodiments of the present disclosure involve using multiple antennas to facilitate the reliable reception of wireless input signals at the analyte sensor system. For example, in certain situations, it may be difficult to reliably receive wireless input signals using the antenna associated with the analyte sensor system. This may be due to, among other factors, a distance between the source of the wireless input signal and the antenna associated with the analyte sensor system, scattering effects, reflection, interference, power management or radiation considerations, etc. Accordingly, in embodiments, one or more additional antennas may be used to receive a wireless input signal from an external source and further to transmit (or radiate) a modified version of the wireless input signal to the analyte sensor system. The analyte sensor system may then receive the modified version of the wireless input signal (e.g., using an associated antenna) and use the modified version of the wireless input signal for purposes of activation/triggering, pairing, and/or exchanging analyte information.

One aspect of the present disclosure includes a system for wireless communication of analyte information. The system may include an analyte sensor system. The analyte sensor system may include an analyte sensor adapted to gather information related to a level of an analyte in a host. The analyte sensor system may include analyte sensor electronics circuitry adapted to transmit and receive wireless signals using a first antenna. The analyte sensor is electrically and mechanically coupled to the analyte sensor electronics circuitry before the analyte sensor system is transitioned into an operational state. The analyte sensor system may include a second antenna adapted to receive an input signal from a source external to the analyte sensor system and further adapted to transmit a modified signal generated using the input signal. The analyte sensor electronics circuitry is further adapted to use the first antenna to receive the modified signal. The analyte sensor system is further adapted to transition into the operational state in response to the modified signal received using the first antenna.

In certain implementations, which may be generally applicable but are also particularly applicable in connection with this aspect of the present disclosure, the second antenna is mechanically coupled to an applicator or packaging for the analyte sensor system.

In implementations, the second antenna is mechanically coupled to the analyte sensor system.

In some implementations, the second antenna is mechanically coupled to a housing of the analyte sensor system.

In implementations, at least a portion of the second antenna is internal to the analyte sensor system relative to a housing of the analyte sensor system.

In some implementations, at least a portion of the second antenna is external to the analyte sensor system relative to a housing of the analyte sensor system.

In implementations, at least a portion of the second antenna resides within a housing of the analyte sensor system.

In some implementations, the modified signal received using the first antenna comprises pairing information transmitted to the analyte sensor system for purposes of connection establishment.

In implementations, the modified signal received using the first antenna comprises information transmitted to the analyte sensor system for purposes of exchanging the information related to the level of the analyte in the host.

Additional aspects of the present disclosure include a method of wireless communication using an analyte sensor system. The analyte sensor system may include an analyte sensor and analyte sensor electronics circuitry. The analyte sensor is adapted to gather information related to a level of an analyte in a host. The analyte sensor is mechanically and electronically coupled to the analyte sensor electronics circuitry before the analyte sensor system is transitioned into an operational state. The analyte sensor electronics circuitry is adapted to transmit and receive wireless signals using a first antenna. The method may include one or more operations. One such operation is a second antenna receiving an input signal from a source external to the analyte sensor system. Another such operation is generating a modified signal using the input signal received from the source. Yet another such operation is the second antenna transmitting the modified signal to the analyte sensor system. Another such operation is the analyte sensor electronics circuitry using the first antenna to receive the modified signal transmitted by the first antenna.

In certain implementations the method includes another operation. The operation is the analyte sensor system transitioning into the operational state in response to the modified signal received using the first antenna.

BRIEF DESCRIPTION OF THE DRAWINGS

Further aspects of the present disclosure will be more readily appreciated upon review of the detailed description of the various disclosed embodiments, described below, when taken in conjunction with the accompanying figures.

The figures are described in greater detail below. Examples described in connection with the figures are provided for purposes of illustration only, and merely depict embodiments of the disclosure. The figures are not intended to be exhaustive or to limit the disclosure to the precise form disclosed. It should also be understood that the disclosure may cover modifications or alterations to features disclosed herein.

DETAILED DESCRIPTION

Embodiments of the present disclosure are directed to systems, methods, devices, and the like that may be used for wireless communication of analyte data. In various deployments described herein, the analyte data is glucose data generated by an analyte sensor system configured to connect to display devices, partner devices (e.g., medical devices such as an insulin pump), other remote connectable devices, and the like. Implementing aspects of the present disclosure, including more particularly, the systems, methods, apparatuses, devices, etc. described herein that provide increased robustness against false or otherwise undesired activation, wakeups, and/or related mode or state changes, or the like, for components of an analyte sensor system, may improve the accuracy, robustness, and/or power management of the analyte sensor system in wireless communications with a display device, one or more partner devices, and/or other (e.g., electronic) devices. Moreover, implementing aspects of the present disclosure may also allow for improving performance with respect to longevity and usability of the analyte sensor system. Aspects of the present disclosure further include using multiple antennas to facilitate the reception of wireless input signals at an analyte sensor system.

The details of some example embodiments of the systems, methods, and devices of the present disclosure are set forth in this description and in some cases, in other portions of the disclosure. Other features, objects, and advantages of the disclosure will be apparent to one of skill in the art upon examination of the present disclosure, description, figures, examples, and claims. It is intended that all such additional systems, methods, devices, features, and advantages may be included within this description (whether explicitly or by reference), may be within the scope of the present disclosure, and may be protected by one or more of the accompanying claims.

A. System Overview & Example Configurations

Figure 1:
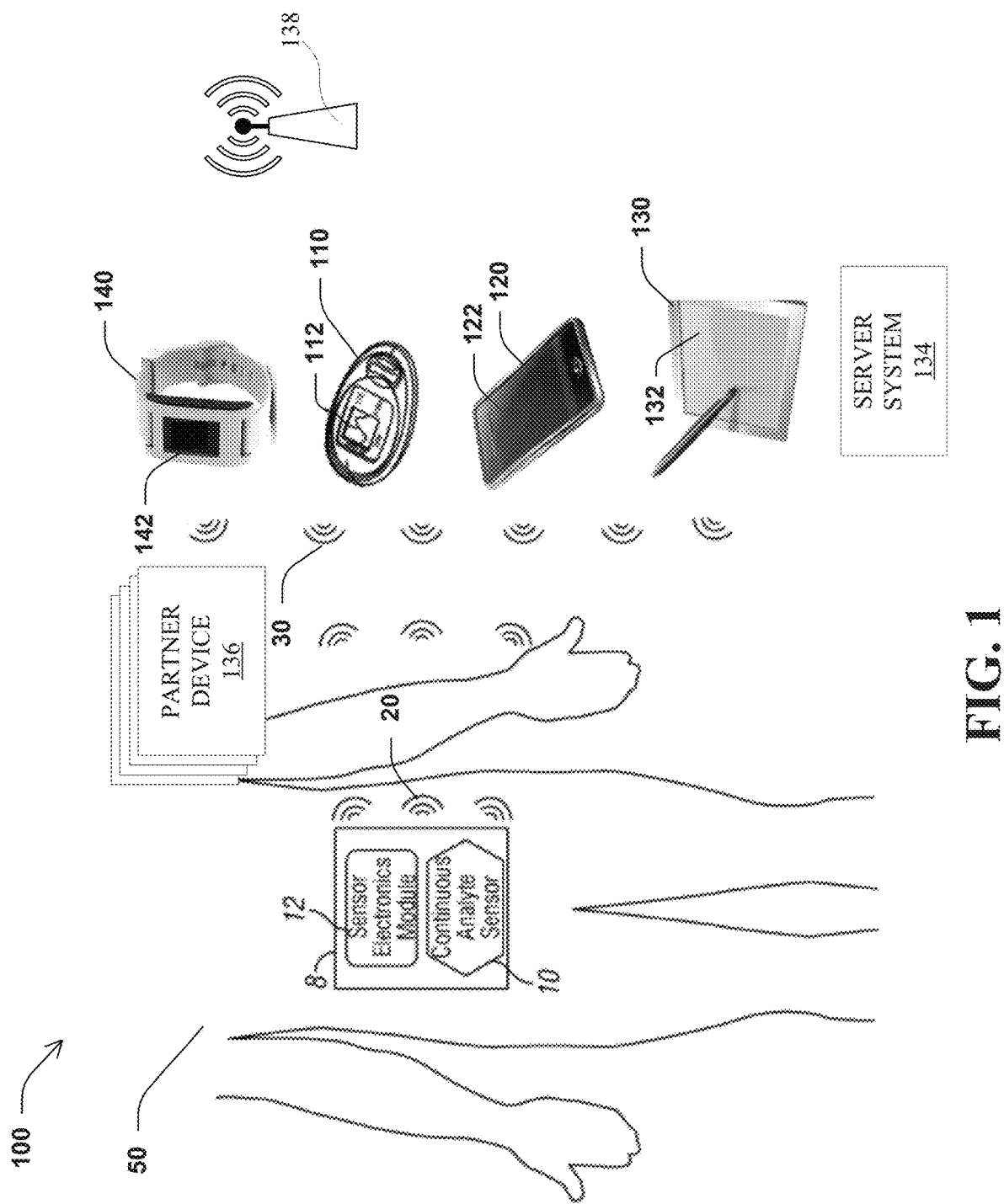
FIG. 1 illustrates aspects of an example system that may be used in connection with implementing embodiments of the disclosure.

FIG. 1 depicts system 100 that may be used in connection with embodiments of the present disclosure that may involve or relate to gathering, monitoring, and/or providing information regarding analyte values present in a user's body, including for example the user's blood glucose values. System 100 depicts aspects of analyte sensor system 8 that may be communicatively coupled to display devices 110, 120, 130, and 140, partner devices 136, and/or server system 134.

Analyte sensor system 8 in the illustrated embodiment includes analyte sensor electronics module 12 and analyte sensor 10 associated with analyte sensor electronics module 12. Analyte sensor electronics module 12 may be electrically and mechanically coupled to analyte sensor 10 before analyte sensor 10 is implanted in a user or host. Accordingly, analyte sensor 10 may not require a user to couple analyte sensor electronics module 12 to analyte sensor 10. For example, analyte sensor electronics module 12 may be physically/mechanically and electrically coupled to analyte sensor 10 during manufacturing, and this physical/mechanical and electrical connection may be maintained during shipping, storage, insertion, use, and removal of analyte sensor system 8. As such, the electro-mechanically connected components (e.g., analyte sensor 10 and analyte sensor electronics module 12) of analyte sensor system 8 may be referred to as a "preconnected" system. Analyte sensor electronics module 12 may be in wireless communication (e.g., directly or indirectly) with one or more of display devices 110, 120, 130, and 140. In addition or alternatively to display devices 110, 120, 130, and 140, analyte sensor electronics module 12 may be in wireless communication (e.g., directly or indirectly) with partner devices 136 and/or server system 134. Likewise, in some examples, display devices 110-140 may additionally or alternatively be in wireless communication (e.g., directly or indirectly) with partner devices 136 and/or server system 134. Various couplings shown in FIG. 1 can be facilitated with wireless access point 138, as also mentioned below.

In certain embodiments, analyte sensor electronics module 12 includes electronic circuitry associated with measuring and processing analyte sensor data or information, including prospective algorithms associated with processing and/or calibration of the analyte sensor data/information. Analyte sensor electronics module 12 can be physically/mechanically connected to analyte sensor 10 and can be integral with (non-releasably attached to) or releasably attachable to analyte sensor 10. Analyte sensor electronics module 12 may also be electrically coupled to analyte sensor 10, such that the components may be electromechanically coupled to one another. Analyte sensor electronics module 12 may include hardware, firmware, and/or software that enables measurement and/or estimation of levels of the analyte in a host/user via analyte sensor 10 (e.g., which may be/include a glucose sensor). For example, analyte sensor electronics module 12 can include one or more of a potentiostat, a power source for providing power to analyte sensor 10, other components useful for signal processing and data storage, and a telemetry module for transmitting data from the sensor electronics module to one or more display devices. Electronics can be affixed to a printed circuit board (PCB) within analyte sensor system 8, or platform or the like, and can take a variety of forms. For example, the electronics can take the form of an integrated circuit (IC), such as an Application-Specific Integrated Circuit (ASIC), a microcontroller, and/or a processor.

Analyte sensor electronics module 12 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entireties.

With further reference to FIG. 1, display devices 110, 120, 130, and/or 140 can be configured for displaying (and/or alarming) displayable sensor information that may be transmitted by sensor electronics module 12 (e.g., in a customized data package that is transmitted to the display devices based on their respective preferences). Each of display devices 110, 120, 130, or 140 can (respectively) include a display such as touchscreen display 112, 122, 132,/or 142 for displaying sensor information and/or analyte data to a user and/or receiving inputs from the user. For example, a graphical user interface (GUI) may be presented to the user for such purposes. In embodiments, the display devices may include other types of user interfaces such as voice user interface instead of or in addition to a touchscreen display for communicating sensor information to the user of the display device and/or receiving user inputs. In embodiments, one, some, or all of display devices 110, 120, 130, 140 may be configured to display or otherwise communicate the sensor information as it is communicated from sensor electronics module 12 (e.g., in a data package that is transmitted to respective display devices), without any additional prospective processing required for calibration and/or real-time display of the sensor data.

The plurality of display devices 110, 120, 130, 140 depicted in FIG. 1 may include a custom display device, for example, analyte display device 110, specially designed for displaying certain types of displayable sensor information associated with analyte data received from sensor electronics module 12 (e.g., a numerical value and/or an arrow, in embodiments). In embodiments, one of the plurality of display devices 110, 120, 130, 140 includes a smartphone, such as mobile phone 120, based on an Android, iOS, or other operating system, and configured to display a graphical representation of the continuous sensor data (e.g., including current and/or historic data).

As further illustrated in FIG. 1 and mentioned above, system 100 may also include wireless access point (WAP) 138 that may be used to couple one or more of analyte sensor system 8, the plurality display devices 110, 120, 130, 140 etc., server system 134, and medical device 136 to one another. For example, WAP 138 may provide WiFi and/or cellular or other wireless connectivity within system 100. Near Field Communication (NFC) may also be used among devices of system 100 for exchanging data, as well as for performing specialized functions, e.g., waking up or powering a device or causing the device (e.g., analyte sensor electronics module 12 and/or a transmitter) to exit a lower power mode or otherwise change states and/or enter an operational mode. In embodiments, a booster antenna, as will be described herein, may boost signals used for activations, such as, for example, NFC signals. In some cases, NFC or other wireless range or other characteristics may not be sufficient to effectively reach an antenna of analyte sensor system 8, for example when analyte sensor system 8 is inside an applicator. In such cases, an antenna which may in certain instances be a sympathetic antenna or the like, can be added to the outside of the applicator or in another location, as described herein, to boost a signal from the external source/device to enable a local antenna to better receive the signaling from the external source/device. While described with relation to FIG. 1, it will be appreciated that the above boosting of signals may be applied for different use cases, as described in various embodiments herein. Server system 134 may be used to collect analyte data from analyte sensor system 8 and/or the plurality of display devices, for example, to perform analytics thereon, generate universal or individualized models for glucose levels and profiles, provide services or feedback, including from individuals or systems remotely monitoring the analyte data, and so on. Partner device(s) 136, by way of overview and example, can usually communicate (e.g., wirelessly) with analyte sensor system 8, including for authentication of partner device(s) 136 and/or analyte sensor system 8, as well as for the exchange of analyte data, medicament data, other data, and/or control signaling or the like. Partner devices 136 may include a passive device in example embodiments of the disclosure. One example of partner device 136 may be an insulin pump for administering insulin to a user in response and/or according to an analyte level of the user as measured/approximated using analyte sensor system 8. For a variety of reasons, it may be desirable for such an insulin pump to receive and track glucose values transmitted from analyte sensor system 8 (with reference to FIG. 1 for example). One example reason for this is to provide the insulin pump a capability to suspend/activate/control insulin administration to the user based on the user's glucose value being below/above a threshold value.

Figure 2:
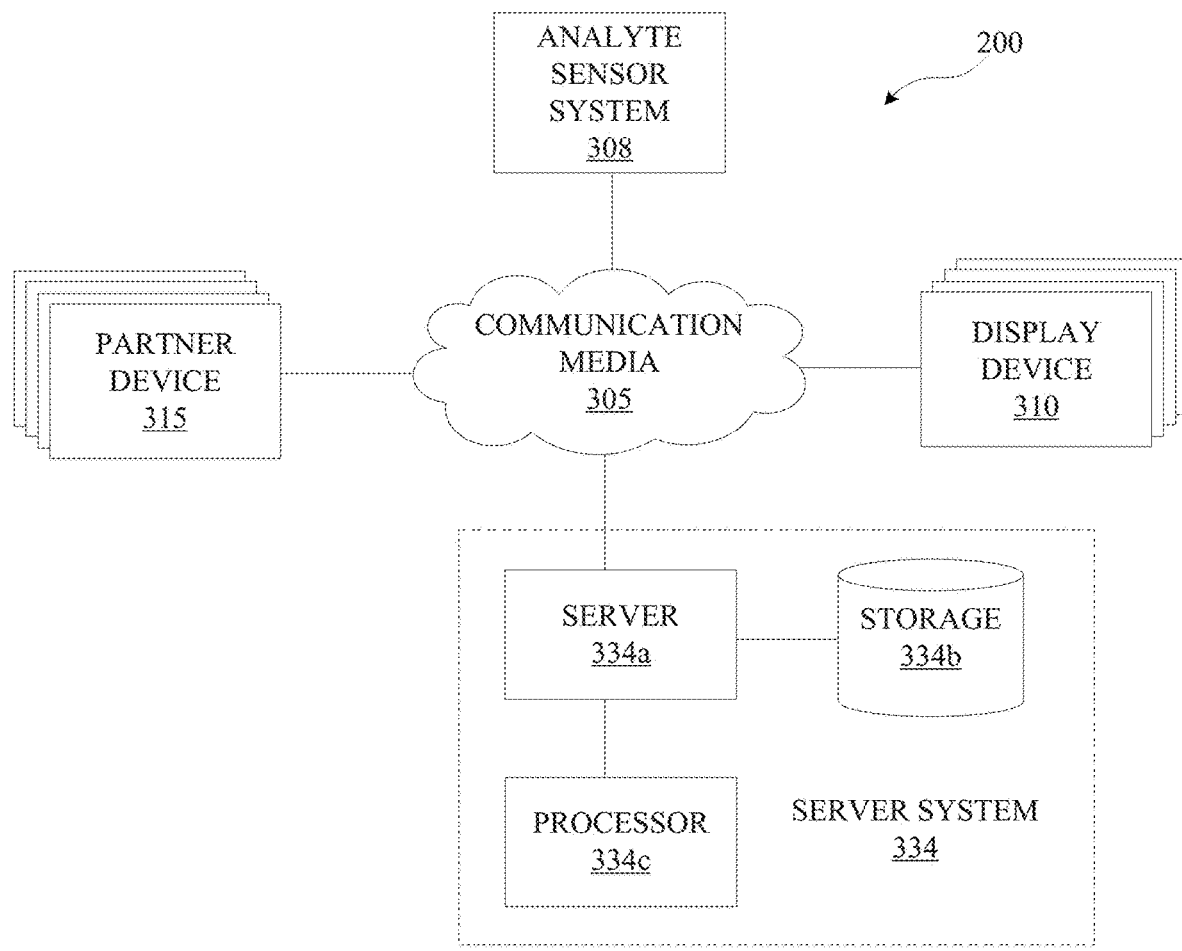
FIG. 2 illustrates aspects of an example system that may be used in connection with implementing embodiments of the disclosure.

Referring now to FIG. 2, system 200 is depicted. System 200 may be used in connection with implementing embodiments of the disclosed systems, methods, apparatuses, and/or devices, including, for example, aspects described above in connection with FIG. 1. By way of example, various below-described components of FIG. 2 may be used to provide wireless communication of analyte (e.g., glucose) data, for example among/between analyte sensor system 308, display devices 310, partner devices 315, and/or one or more server systems 334, and so on.

As shown in FIG. 2, system 200 may include analyte sensor system 308, one or more display devices 310, and/or one or more partner devices 315. Additionally, in the illustrated embodiment, system 200 includes server system 334, which can in turn includes server 334a coupled to processor 334c and storage 334b. Analyte sensor system 308 may be coupled to display devices 310, partner devices 315, and/or server system 334 via communication media 305. Some details of the processing, gathering, and exchanging of data, and/or executing actions (e.g., providing medicaments or related instructions) by analyte sensor system 308, partner devices 315, and/or display device 310, etc., are provided below.

Analyte sensor system 308, display devices 310, and/or partner devices 315 may exchange messaging (e.g., control signaling) via communication media 305, and communication media 305 may also be used to deliver analyte data to display devices 310, partner devices 315, and/or server system 334. As alluded to above, display devices 310 may include a variety of electronic computing devices, such as, for example, a smartphone, tablet, laptop, wearable device, etc. Display devices 310 may also include analyte display device 110 that may be customized for the display and conveyance of analyte data and related notifications etc. Partner devices 315 may include medical devices, such as an insulin pump or pen, connectable devices, such as a smart fridge or mirror, key fob, and other devices.

In embodiments, communication media 305 may be based on one or more wireless communication protocols, such as for example Bluetooth, Bluetooth Low Energy (BLE), Zig-Bee, WiFi, IEEE 802.11 protocols, Infrared (IR), Radio Frequency (RF), 2G, 3G, 4G, 5G, etc., and/or wired protocols and media. It will also be appreciated upon studying the present disclosure that communication media can be implemented as one or more communication links, including in some cases, separate links, between the components of system 200, whether or not such links are explicitly shown in FIG. 2 or referred to in connection therewith. By way of illustration, analyte sensor system 308 may be coupled to display device 310 via a first link of communication media 305 using BLE, while display device 310 may be coupled to server system 334 by a second link of communication media 305 using a cellular communication protocol (e.g., 4G LTE/5G and the like). In embodiments, a BLE signal may be temporarily attenuated to minimize data interceptions. For example, attenuation of a BLE signal through hardware or firmware design may occur temporarily during moments of data exchange (e.g., pairing).

In embodiments, the elements of system 200 may be used to perform operations of various processes described herein and/or may be used to execute various operations and/or features described herein with regard to one or more disclosed systems and/or methods. Upon studying the present disclosure, one of skill in the art will appreciate that system 200 may include single or multiple analyte sensor systems 308, communication media 305, and/or server systems 334.

As mentioned, communication media 305 may be used to connect or communicatively couple analyte sensor system 308, display devices 310, partner devices 315, and/or server system 334 to one another or to a network. Communication media 305 may be implemented in a variety of forms. For example, communication media 305 may include one or more of an Internet connection, such as a local area network (LAN), a person area network (PAN), a wide area network (WAN), a fiber optic network, internet over power lines, a hard-wired connection (e.g., a bus), DSL, and the like, or any other kind of network connection or communicative coupling. Communication media 305 may be implemented using any combination of routers, cables, modems, switches, fiber optics, wires, radio (e.g., microwave/RF, AM, FM links etc.), and the like. Further, communication media 305 may be implemented using various wireless standards, such as Bluetooth®, BLE, WiFi, IEEE 802.11, 3GPP standards (e.g., 2G GSM/GPRS/EDGE, 3G UMTS/CDMA2000, or 4G LTE/LTE-A/LTE-U, 5G, or subsequent generation), etc. Upon reading the present disclosure, one of skill in the art will recognize other ways to implement communication media 305 for communications purposes, and will also recognize that communication media 305 may be used to implement features of the present disclosure using as of yet undeveloped communications protocols that may be deployed in the future.

Further referencing FIG. 2, server 334a may receive, collect, and/or monitor information, including analyte data, medicament data, and related information, from analyte sensor system 308, partner devices 315 and/or display devices 310, such as input responsive to the analyte data or medicament data, or input received in connection with an analyte monitoring application running on analyte sensor system 308 or display device 310, or a medicament delivery application running on display device 310 or partner device 315. As such, server 334a may receive, collect, and/or monitor information from partner devices 315, such as, for example, information related to the provision of medicaments to a user and/or information regarding the operation of one or more partner devices 315. Server 334a may also receive, collect, and/or monitor information regarding a user of analyte sensor system 308, display devices 310, and/or partner devices 315.

In embodiments, server 334a may be adapted to receive such information via communication media 305. This information may be stored in storage 334b and may be processed by processor 334c. For example, processor 334c may include an analytics engine capable of performing analytics on information that server 334a has collected, received, etc. via communication media 305. In embodiments, server 334a, storage 334b, and/or processor 334c may be implemented as a distributed computing network, such as a Hadoop® network, or as a relational database or the like. The aforementioned information may then be processed at server 334a such that services may be provided to analyte sensor system 308, display devices 310, partner devices 315, and/or a user(s) thereof. For example, such services may include diabetes management feedback for the user.

In embodiments, a database may be implemented in server system 334 that may pair user accounts to one or more analyte sensor systems 308 using communication media 305. Based on, for example, an expected lifetime of individual components or one or more groups of components of analyte sensor system 308, or analyte sensor system 308 as a whole, and/or based on diagnostic feedback received by analyte sensor system 308, server system 334 may be able to determine if a given analyte sensor system 308 or component or group(s) of components thereof is expired or passed its useful life. A user may receive an indication, notification, alert, or warning, for example, on display device 310 and/or through analyte sensor system 308, from server system 334, that analyte sensor system 308 or a component or group(s) of components thereof has expired or passed its useful life or will do so soon or within a given amount of time. In embodiments, a user may receive an indication, notification, alert, or warning on display device 310 from server system 334 about the expected lifetime of analyte sensor system 308 or a component or group(s) of components thereof.

Server 334a may include, for example, an Internet server, a router, a desktop or laptop computer, a smartphone, a tablet, a processor, a module, or the like, and may be implemented in various forms, including, for example, an integrated circuit or collection thereof, a printed circuit board or collection thereof, or in a discrete housing/package/rack or multiple of the same. In embodiments, server 334a at least partially directs communications made over communication media 305. Such communications may include the delivery of analyte data, medicament data, and/or messaging related thereto (e.g., advertisement, authentication, command, or other messaging). For example, server 334a may process and exchange messages between and/or among analyte sensor system 308, display devices 310, and/or partner devices 315 related to frequency bands, timing of transmissions, security/encryption, alarms, alerts, notifications, and so on. Server 334a may update information stored on analyte sensor system 308, partner devices 315, and/or display devices 310, for example, by delivering applications thereto or updating the same, and/or by reconfiguring system parameters or other settings of analyte sensor system 308, partner devices 315, and/or display devices 310. Server 334a may send/receive information to/from analyte sensor system 308, partner devices 315, and/or display devices 310 in real time, periodically, sporadically, or on an event-drive basis. Further, server 334a may implement cloud computing capabilities for analyte sensor system 308, partner devices 315, and/or display devices 310.

With the above description of aspects of the presently disclosed systems and methods for wireless communication of analyte data, examples of some specific features of the present disclosure will now be provided. It will be appreciated by one of skill in the art upon studying the present disclosure that these features may be implemented using aspects and/or combinations of aspects of the example configurations described above, whether or not explicit reference is made to the same.

B. Analyte Data

Referring back to FIG. 1, as mentioned above, in embodiments, analyte sensor system 8 is provided for measurement of an analyte in a host or user. By way of an overview and an example, analyte sensor system 8 may be implemented as an encapsulated microcontroller that makes sensor measurements, generates analyte data (e.g., by calculating values for continuous glucose monitoring data), and engages in wireless communications (e.g., via Bluetooth and/or other wireless protocols) to send such data to remote devices (e.g., display devices 110, 120, 130, 140, partner devices 136, and/or server system 134).

Analyte sensor system 8 may include: analyte sensor 10 configured to measure a concentration or level of the analyte in the host, and analyte sensor electronics module 12 that is typically physically connected to analyte sensor 10 before analyte sensor 10 is implanted in a user. In embodiments, analyte sensor electronics module 12 includes electronics configured to process a data stream associated with an analyte concentration measured by analyte sensor 10, in order to generate sensor information that includes raw sensor data, transformed sensor data, and/or any other sensor data, for example. Analyte sensor electronics module 12 may further be configured to generate analyte sensor information that is customized for respective display devices 110, 120, 130, 140, partner devices 136, and/or server system 134. Analyte sensor electronics module 12 may further be configured such that different devices may receive different sensor information, and may further be configured to wirelessly transmit sensor information to such display devices 110, 120, 130, 140, partner devices 136, and/or server system 134.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

C. Preconnected Analyte Sensor System

As alluded to above with reference to FIG. 1, in embodiments, analyte sensor 10 includes a continuous glucose sensor, for example, a subcutaneous, transdermal (e.g., transcutaneous), or intravascular device. In embodiments, such a sensor or device can analyze a plurality of intermittent blood samples. Analyte sensor 10 can use any method of analyte measurement, including for example glucose-measurement, including enzymatic, chemical, physical, electrochemical, spectrophotometric, polarimetric, calorimetric, iontophoretic, radiometric, immunochemical, and the like.

In embodiments where analyte sensor 10 is a glucose sensor, analyte sensor 10 can use any method, including invasive, minimally invasive, and non-invasive sensing techniques (e.g., fluorescence monitoring), or the like, to provide a data stream indicative of the concentration of glucose in a host. The data stream may be a raw data signal, which may be converted into a calibrated and/or filtered data stream that can be used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. According to one example embodiment described below, an implantable glucose sensor may be used. However, it should be understood that the devices and methods described herein can be applied to any device capable of detecting a concentration of an analyte, glucose for example, and providing an output signal that represents the concentration of the analyte, again glucose for example (e.g., as a form of analyte data).

In embodiments, analyte sensor 10 is an implantable glucose sensor, such as described with reference to U.S. Pat.

No. 6,001,067 and U.S. Patent Publication No. US-2005-0027463-A1. In embodiments, analyte sensor 10 is a transcutaneous glucose sensor, such as described with reference to U.S. Patent Publication No. US-2006-0020187-A1. In embodiments, analyte sensor 10 is configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007. In embodiments, the continuous glucose sensor includes a transcutaneous sensor such as described in U.S. Pat. No. 6,565,509 to Say et al., for example. In embodiments, analyte sensor 10 is a continuous glucose sensor that includes a subcutaneous sensor such as described with reference to U.S. Pat. No. 6,579,690 to Bonnecaze et al. or U.S. Pat. No. 6,484,046 to Say et al., for example. In embodiments, the continuous glucose sensor includes a refillable subcutaneous sensor such as described with reference to U.S. Pat. No. 6,512,939 to Colvin et al., for example. The continuous glucose sensor may include an intravascular sensor such as described with reference to U.S. Pat. No. 6,477,395 to Schulman et al., for example. The continuous glucose sensor may include an intravascular sensor such as described with reference to U.S. Pat. No. 6,424,847 to Mastrototaro et al., for example.

In systems that are not preconnected, analyte sensor 10 and analyte sensor electronics module 12 are usually mechanically and electrically connected for the first time after analyte sensor 10 is implanted into the user. Electrodes of analyte sensor electronics module 12 are typically monitored to detect an analyte related signal when analyte sensor electronics module 12 is coupled to an already implanted analyte sensor 10. Analyte sensor system 8 may then be activated in response to the coupling and detection of a particular level or characteristic of analyte in a user. However, in a preconnected analyte sensor system 8, analyte sensor 10 may be electromechanically coupled to analyte sensor electronics module 12 before analyte sensor system 8 is delivered to user and thus analyte sensor electronics module 12 is already coupled to analyte sensor 10 at the time of sensor implantation.

Additionally, accurate detection of the implantation time of analyte sensor 10 can assist in preventing reuse of analyte sensor 10. Detection of sensor implantation time by electronics module 12 can enable a higher reliability metric versus a reliance on the user providing notification of insertion/implantation time. For example, disconnection and/or implantation characteristics can distinguish a newly inserted analyte sensor 10 from an attempt of the user to restart an expired analyte sensor 10.

As an additional example, accurate detection/estimation of analyte sensor 10 implantation time may enable faster connectivity establishment between analyte sensor electronics module 12 and devices connectable thereto (see, e.g., FIG. 1). With a more accurate detection and/or estimation of analyte sensor 10 implantation time, analyte sensor system 8 may be placed in a state to establish and enter into communication with multiple devices based on being near to or at the time of implantation. For example, analyte sensor system 8 may be able to enter a pairing state within a relatively short time of implantation (e.g., less than 10 to 15 minutes) such that display devices (e.g., display devices 110, 120, 130, 140, partner device(s) 136, etc., referencing FIG. 1 by way of example) may be able to wirelessly connect to analyte sensor system 8. A more accurate detection of analyte sensor 10 implantation time may also be used to trigger alternative connection profiles to encourage faster connection, for example, pairing, encryption, advertisement characteristics, etc. That is, for example, a more definitive wakeup event can be used to facilitate a more aggressive connection model as between analyte sensor system 8 and a device connectable thereto (e.g., sending advertisement packets at a faster rate or the like). This may enable faster connection establishment, and may also provide the user with near real time feedback that analyte sensor system 8 is receiving a signal and is connected to the display device.

Figure 3A:
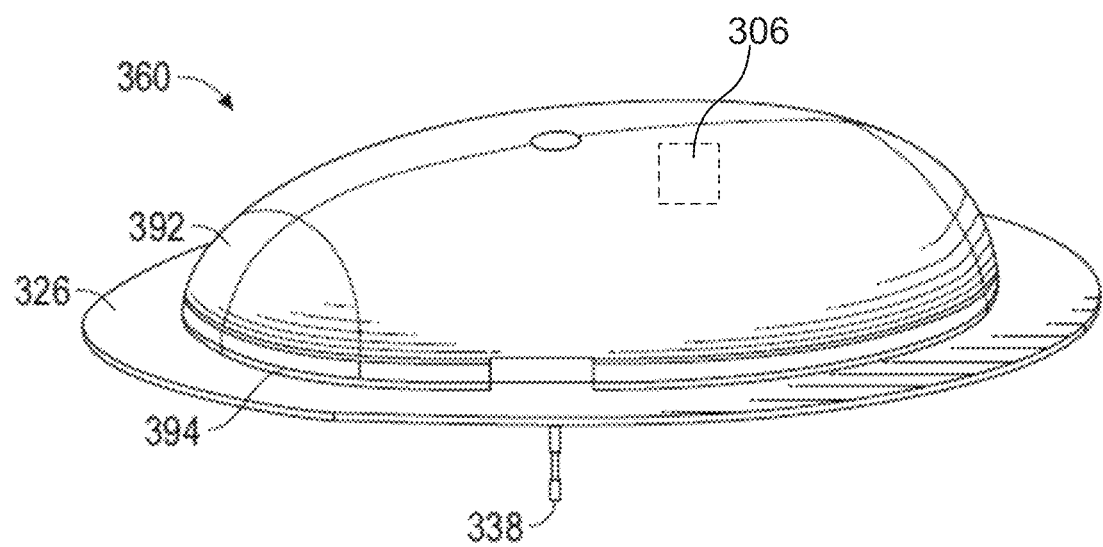
FIG. 3A is an example analyte sensor system according to embodiments of the present disclosure.

FIG. 3A illustrates a perspective view of an on-skin sensor assembly 360 that may be used in connection with a pre-connected analyte sensor system 8, in accordance with some embodiments. For example, on-skin analyte sensor assembly 360 may be or include at least aspects of analyte sensor system 8, with reference by way of example to FIG. 1, and/or analyte sensor system 308, with reference by way of example to FIG. 5. On-skin sensor assembly 360 may include an outer housing. In embodiments, the outer housing may include a first, top portion 392 and a second, lower portion 394. In embodiments, the outer housing may include a clamshell or other design. The outer housing may feature a generally oblong shape. The outer housing may further include aperture 396 disposed substantially through a center portion of outer housing and adapted for sensor 338 and needle insertion through a bottom of on-skin sensor assembly 360. In embodiments, aperture 396 may be a channel or elongated slot. On-skin sensor assembly 360 may further include an adhesive patch 326 configured to secure on-skin sensor assembly 360 to skin of the host. In embodiments, adhesive patch 326 may include an adhesive suitable for skin adhesion, for example a pressure sensitive adhesive (e.g., acrylic, rubber-based, or other suitable type) bonded to a carrier substrate (e.g., spun lace polyester, polyurethane film, or other suitable type) for skin attachment, though any suitable type of adhesive is also contemplated. As shown, adhesive patch 326 may feature an aperture 398 aligned with aperture 396 such that sensor 338 may pass through a bottom of on-skin sensor assembly 360 and through adhesive patch 326.

On-skin sensor assembly 360 may include, for example, similar components as analyte sensor electronics module 12 described above in connection with FIG. 1, for example, a potentiostat, a power source for providing power to analyte sensor 10, signal processing components, data storage components, and a communication module (e.g., a telemetry module; transmitter, receiver, and/or transceiver circuits; etc.) that may be used for one-way or two-way data communication, a printed circuit board (PCB), an integrated circuit (IC), an Application-Specific Integrated Circuit (ASIC), a microcontroller, and/or a processor.

Additionally, on-skin assembly 360 may include antenna 306. In embodiments, antenna 306 can be wirelessly coupled to on-skin assembly 360. In embodiments, on-skin assembly 360 includes a second antenna (not shown in FIG. 3A, but may be similar to antenna 412 with reference to FIG. 4 and antenna 512 with reference to FIG. 5) that may be electrically coupled (e.g., hardwired) to one or more electronics components that may be used in connection with and/or included within on-skin assembly 360. In one example, a feed of the second antenna may be electrically coupled to transmission/reception circuitry used in connection with on-skin assembly 360. The second antenna may exchange signals wirelessly with antenna 306, such that signals transmitted using antenna 306 may be processed by the one or more electronics components and/or such that signals generated using the one or more electronics components can be received using antenna 306. In some embodiments, the second antenna could be a passive antenna (e.g., a concentrator) that re-radiates the received input signal and is not electrically coupled to the one or more electronics components. In embodiments, the second antenna may be implemented on one or more bodies of the on-skin assembly. The second antenna may be electrically coupled to a body of the on-skin assembly, other than the body containing the transceiver circuit (e.g., adhesive patch, housing, etc.). For example, portion(s) of the second antenna can be placed on, integrated within, affixed to, and/or coupled to adhesive patch 396. In such examples, radiating elements and/or other portion(s) of the second antenna may be implemented using skin adhesive patch 326. It should also be appreciated that in some cases, portion(s) of antenna 306 may alternatively or additionally be implemented using adhesive patch 326.

Antenna 306 may be any type of antenna. For example, antenna 306 may be, use, or include a dipole antenna, fractal antenna, loop antenna, monopole antenna, aperture antenna, traveling wave antenna, whip antenna, array of conductors, phased array (e.g., broadside array or end-fire array), and/or any other component that serves as an interface between radio waves propagating through space (or other dielectric) and electric currents (e.g., that may flow in conductors etc.). In various embodiments, antenna 306 may be omnidirectional or may be directional or high gain. Antenna 306 may include parasitic elements, parabolic reflectors or horns, baffles, or other components that may be used to control the directionality or radiation pattern of the antenna. Antenna 306 may be implemented in an integrated circuit, or may be formed from one or more discrete components. A ground plane or other implementation of antenna counterpoise(s) may be used in connection with antenna 306. In embodiments, the host may be used to form a ground plane. For example, one or more body parts of the host may be used to form such a ground plane that may be used to adjust a directionality associated with antenna 306. More generally, the directionality of antenna 306 may be adjusted to enhance reception of signals originating from certain locations, such as a host's pocket or wrist, an applicator, as will be described herein, or any other location where a signal source may be located (e.g., anywhere the host may keep display device 310). The size and shape of antenna 306 may be adjusted based on various configurations of source devices that may be used. For example, the size or shape or directionality of antenna 306 can be based on various likely or anticipated locations of display device 310 or other signal source.

At this juncture, it should be noted that the antenna that can be electrically coupled to one or more electronics components of on-skin assembly 360 and used in connection with and/or included within on-skin assembly 360 can similarly be any type of antenna. It should further be noted that in some embodiments, one or more switches or other components can be used in connection with on-skin assembly 360 to electrically couple antenna 306 to one or more electronics components of on-skin assembly 360. For example, in certain embodiments, antenna 306 can be selectively wireless or electrically coupled to the one or more electronics components of on-skin assembly 360, and the other antenna (if present) can be selectively bypassed in certain example embodiments. In embodiments, the other antenna may be referred to as a local antenna.

Antenna 306 may receive an input, wireless signals, or RF signals from a source external to on-skin assembly 360, and may further transmit or radiate a modified version of the input or other wireless signal to the local antenna or other locations and/or devices. For example, antenna 306 may be used to effectively boost the received input or other wireless signal as received by the local antenna (again, not shown in FIG. 3A). The modification of the input or other wireless signal by antenna 306 may thus facilitate reception of the signal by the local antenna. The local antenna, may be located, for example, within on-skin assembly 360 or in various other locations discussed herein. Antenna 306 may be a sympathetic antenna implemented using and/or in conjunction with one or more passive and/or active components. In some embodiments, antenna 306 may be implemented on the applicator, as described herein. This may be useful in certain circumstances where the level, amplitude, power, and/or other characteristics (e.g., phase components) of the input or other wireless signal received at the local antenna of on-skin assembly 360 may otherwise be insufficient or not ideal. For example, the input or other wireless signal may be an NFC, BLE, WiFi, cellular, or other wireless signal for which the feasible range or environment for transmission may not always be sufficient or conducive for effectively reaching the local antenna. This may occur under many various conditions. One example of such a condition may occur when on-skin assembly 360 is located inside an applicator thereof, and the external source of the input or other wireless signal is outside the applicator. In such circumstances, for example, antenna 306, one or more passive components, and/or one or more active components (e.g., amplifiers, transistors, etc.) may be used to increase the power of at least relevant aspects of the modified version of the input or other wireless signal transmitted by antenna 306 that may be received at the local antenna (e.g., antenna 412/512 etc.).

In other words, antenna 306, one or more passive components, and/or one or more active components may be used to provide a modification to the input or other wireless signal. For example, antenna 306 and/or such component(s) may provide a modification related to directionality to increase the focus of the input or other wireless signal (e.g., beam steering, phase adjustments, etc.). For example, such component(s) may provide a modification that involves amplification and/or shaping (e.g., filtering) of the input or other wireless signal. As another example, such component(s) may provide a modification that involves other conditioning and/or repeating the transmission of the signal from antenna 306 (where the input or other wireless signal was originally transmitted from the external source).

In embodiments, antenna 306 may be mechanically coupled to on-skin assembly 360, including, for example, to any combination of an outside, inside, or other portion of on-skin assembly 360. In embodiments, antenna 306 may be mechanically coupled to an outer housing of on-skin assembly 360. For example, antenna 306 may be integrated into the outer housing. In this example, antenna 306 may be printed and integrated into a non-conductive outer housing outer housing. Antenna 306 may be integrated using techniques, such as, for example, selectively plating conductive antenna traces on the surface of the housing. In embodiments, a MID (molded interconnect device), a LDS (laser direct structuring), and/or two shot molding are some of the manufacturing technologies that may enable using molded (e.g. injection molding) or cast thermoplastic and thermoset to have conductive (e.g. metalized) features over 2D and/or 3D substrate surfaces. In some embodiments, overmolding a preformed antenna may also be used to integrate an antenna in to the housing. It should be appreciated that other techniques may be used. Conductive traces can be used to form external electrical connections to antenna 306, if any such connections are needed. Alternatively or additionally, antenna 306 may be otherwise affixed (e.g., adhered, bonded, friction fit, clipped, soldered, screwed, or the like) to the outer housing (e.g., to an inner or outer surface of the outer housing or another portion thereof). In embodiments, antenna 306 may be mounted on and/or to a PCB, substrate(s), and/or other components that may be located on and/or within on-skin assembly 360 or otherwise mechanically coupled thereto. In some embodiments, antenna 306 may be separate from the components of on-skin assembly 360, or otherwise uncoupled from the on-skin assembly 360. For example, antenna 306 may be placed on the applicator, and antenna 306 may act as a concentrator of the electromagnetic field, NFC signals, and/or any other signals to provide the signal to the local antenna. The local antenna may be more easily able to receive the signal because the signal was concentrated by antenna 306.

In embodiments, at least a portion of antenna 306 is internal to on-skin assembly 360. For example, relative to the outer housing of on-skin assembly 360, at least a portion of antenna 306 may be internal to on-skin assembly 360. In such examples, the portion(s) of antenna 306 that are located within on-skin assembly 360 may be radiating portions of antenna 306 or other portions thereof (e.g., feeding portions, mounting portions, etc.). Additionally or alternatively, as alluded to above, in embodiments, at least a portion of antenna 306 is external to on-skin assembly 360. For example, relative to the outer housing of on-skin assembly 360, at least a portion of antenna 306 may be external to on-skin assembly 360. In such examples, the portion(s) of antenna 306 that are located external to on-skin assembly 360 may be radiating portions of antenna 306 or other portions thereof (e.g., feeding portions, mounting portions, etc.). Additionally or alternatively, in embodiments, at least a portion of antenna 306 resides within the outer housing of on-skin assembly 360. For example, at least a portion of antenna 306 may be encased or otherwise contained or integrated within a portion of the outer housing of on-skin assembly 360. In such examples, the portion(s) of antenna 306 that may be within the outer housing of on-skin assembly 360 may be radiating portions of antenna 306 or other portions thereof (e.g., feeding portions, mounting portions, etc.).

It should be appreciated that although the outer housing is referenced above, there may be multiple pieces or components of the outer housing (e.g., first, top portion 392 and a second, lower portion 394, referencing FIG. 3A), and portion(s) of antenna 306 may be located in any number of such pieces or components, including being distributed through any number of such pieces or components. In some cases, the above-described examples involve antenna 306 being located relative to another housing of on-skin assembly 360. For example, there may be multiple housings (e.g., an inner housing and an outer housing) for on-skin assembly 360, and portion(s) of antenna 306 may be located relative to one or more of such multiple housings in the above-described fashion. Portion(s) of antenna 306 may also be distributed through any number of such housings for on-skin assembly 360. Furthermore, it should be appreciated that the antenna (not shown in FIG. 3A) that is electrically coupled to one or more electronics components that may be used in connection with and/or included within on-skin assembly 360, can in embodiments be configured in a fashion substantially similar to that described above for antenna 306, In embodiments, antenna 306 is an array that includes one or more separate antennas, and/or the integrated antenna is an array that includes one or more separate antennas. In this manner, variations of MIMO, SIMO, MISO, etc. can be employed in connection with certain features described herein.

Figure 3B:
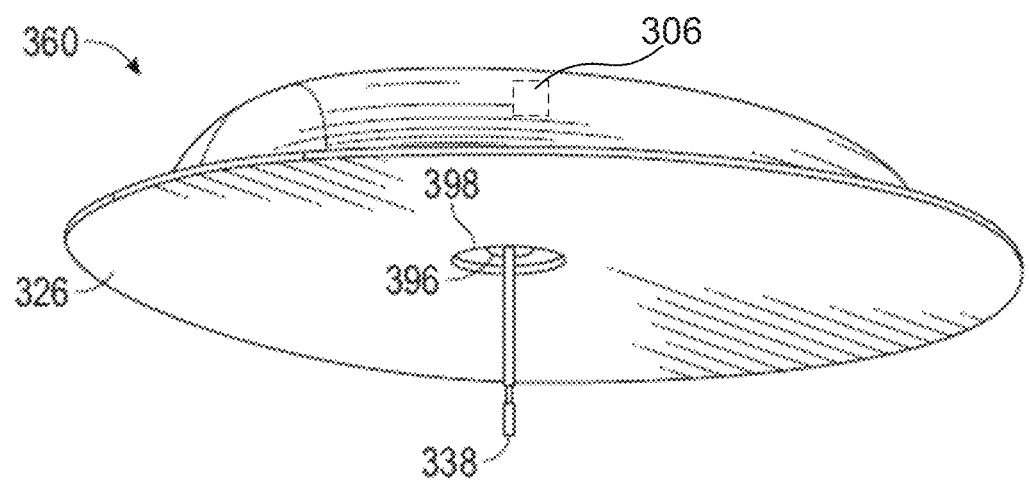
FIG. 3B is an example analyte sensor system according to embodiments of the present disclosure.

FIG. 3B illustrates a bottom perspective view of on-skin sensor assembly 360 of FIG. 3A. FIG. 3B further illustrates aperture 396 disposed substantially in a center portion of a bottom of on-skin sensor assembly 360, and aperture 398, both adapted for sensor 338 and needle insertion.

Figure 4:
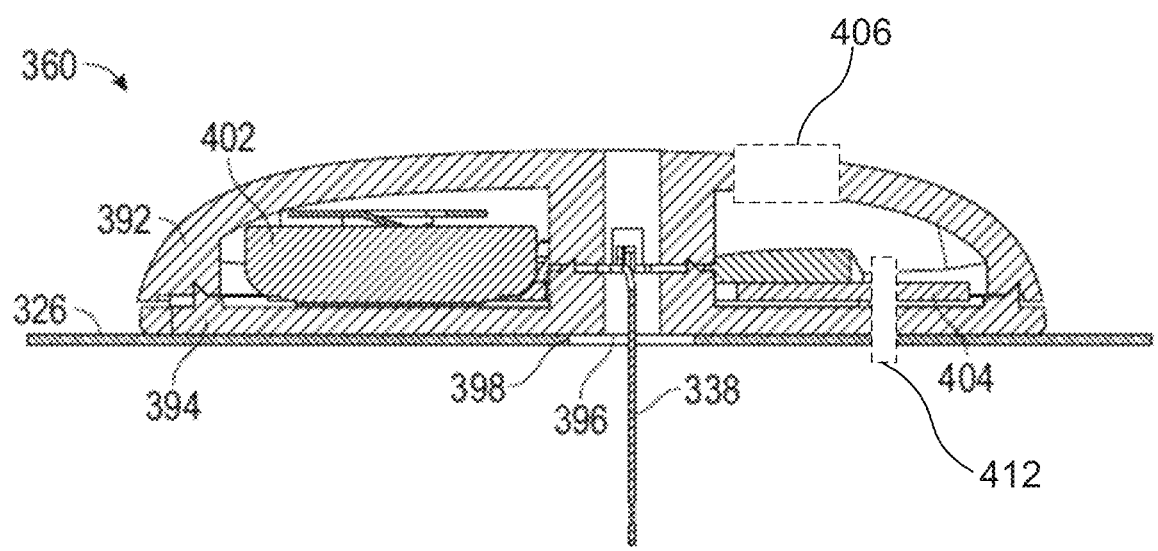
FIG. 4 illustrates aspects of an example analyte sensor system according to embodiments of the disclosure.

FIG. 4 illustrates a cross-sectional view of on-skin sensor assembly 360 of FIGS. 3A and 3B. FIG. 4 illustrates first, top portion 392 and second, bottom portion 394 of the outer housing of on-skin assembly 360, adhesive patch 326, aperture 396 in the center portion of on-skin sensor assembly 360, aperture 398 in the center portion of adhesive patch 326, and sensor 338 passing through aperture 396. The electronics unit, previously described in connection with FIG. 3A, may further include circuit board 404 and battery 402 that may be configured to provide power to at least circuit board 404 and/or certain components connected thereto.

Also shown in FIG. 4 is antenna 406. In embodiments, aspects of antenna 406 may be substantially similar to antenna 306 discussed above in connection with FIGS. 3A and 3B. FIG. 4 also illustrates that on-skin assembly 360 can use antenna 412. Aspects of antenna 412 may be substantially similar to the antenna described above (but not shown) in connection with FIGS. 3A and 3B that can be electrically coupled to one or more electronics components that may be used in connection with and/or included within on-skin assembly 360. Thus, for example, it should be appreciated that one or more portions of antenna 412 can be included in/on and/or implemented in conjunction with adhesive patch 326, circuit board 404 or components connected thereto. Portion(s) of antenna 412 can be included in, on, outside of, and/or or otherwise in conjunction with on-skin assembly 360, for example as described above in connection with certain embodiments involving antenna 306.

Figure 5:
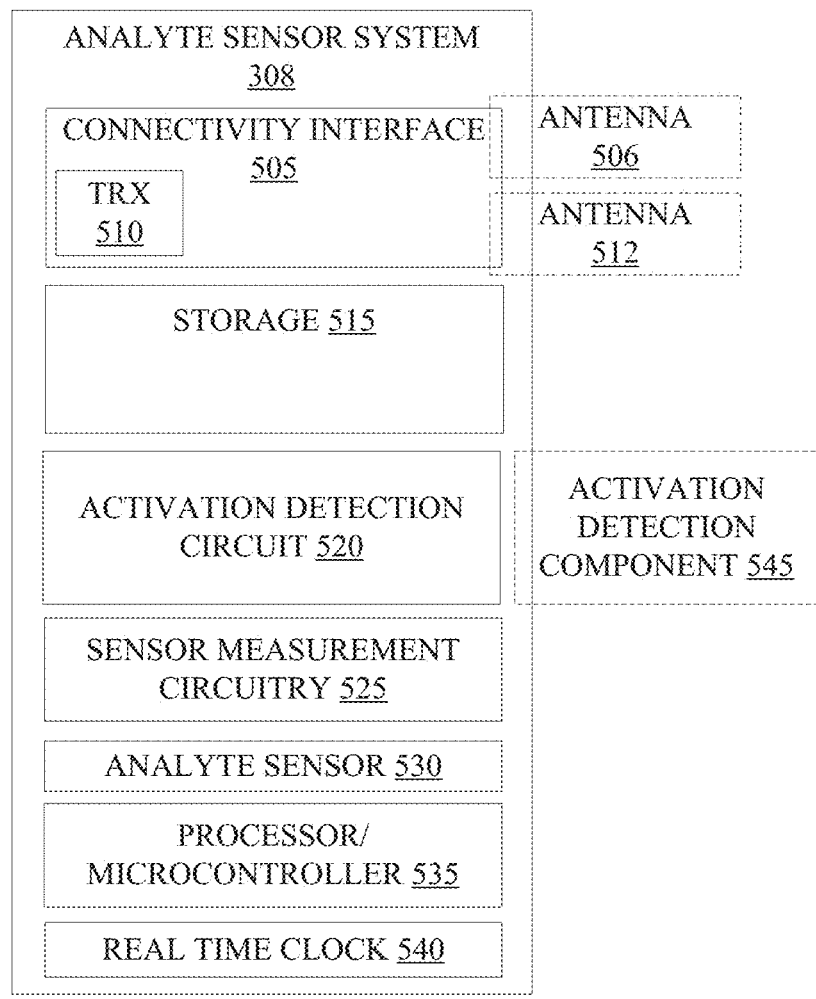
FIG. 5 illustrates aspects of an example analyte sensor system according to embodiments of the disclosure.

Turning now to FIG. 5, a more detailed functional block diagram of analyte sensor system 308 (discussed above, for example, in connection with FIGS. 1 and 2) is provided. As shown in FIG. 5, analyte sensor system 308 may include analyte sensor 530 (e.g., which may also be designated with the numeral 10 in FIG. 1) coupled to analyte sensor measurement circuitry 525 for processing and managing sensor data. Sensor measurement circuitry 525 may be coupled to processor/microprocessor 535 (e.g., which may be part of item 12 in FIG. 1). In some embodiments, processor 535 may perform part or all of the functions of sensor measurement circuitry 525 for obtaining and processing sensor measurement values from analyte sensor 530.

Processor 535 may be further coupled to radio unit 510 (e.g., which may be part of item 12 in FIG. 1) for sending sensor and other data and receiving requests and commands and other signaling from an external device, such as display device 310 (referencing FIG. 2 by way of example). Radio unit 510 may be part of or implemented in conjunction connectivity interface 505. Radio unit 510 may use or include, by way of example, transmitter, receiver, and/or transceiver circuitry. Connectivity interface 505 can be used to interface analyte sensor system 308 to communication media 305, such that analyte sensor system 308 may be communicatively coupled (directly or indirectly) to analyte display device(s) 310, partner device(s) 315, and/or server system 334 via communication media 305. Radio unit 510 of connectivity interface 505 may include one or more transmitter/receiver/transceiver modules operable on different wireless standards and/or frequencies (e.g., including frequency bands).

Additionally, radio unit 510 may use and/or include one or more of antenna 506 and antenna 512. In some embodiments, antenna 506 and/or antenna 512 may not be coupled to the one or more electronic components of analyte sensor system 308. In embodiments, aspects of antenna 506 and antenna 512 may be substantially similar to antenna 406 and 412 described in connection with FIG. 4. Radio unit 510 may be used to send/receive analyte or medicament delivery data, associated commands and messages, and/or other signaling (e.g., that may be used in connection with controlling an operation state, pairing, or other aspects of analyte sensor system 308) to/from analyte sensor system 308, as well as to wirelessly communicate with other devices/nodes via communication media 305. Additionally, connectivity interface 505 may in some cases include additional components for controlling radio and/or other wireless connections, such as baseband and/or WiFi modems, audio/video codecs, and so on.

Processor 535 may include processor sub-modules, including, by way of example, an applications processor and/or other circuitry that interfaces with and/or controls other elements of analyte sensor system 308 (e.g., connectivity interface 505). Processor 535 may be coupled (e.g., by a bus) to connectivity interface 505 and storage 515. Hence, processor 535 may receive and process electrical signals generated by or using these respective elements, including, for example, one or more of antenna 506 and antenna 512, and thus perform various functions. By way of example, processor 535 may access stored content from storage 515 in response to code or other instructions stored on storage 515 or elsewhere within analyte sensor system 308 and process the stored content for transmission via connectivity interface 505 and communication media 305 to display device(s) 310, server system 334, and/or partner device(s) 315. By way of further example, processor 535 may also, in response to code or other instructions stored on storage 515 or elsewhere within analyte sensor system 308, use circuitry of connectivity interface 505 to process information received using one or more of antenna 506 and antenna 512 to condition such information for use by other components of analyte sensor system 308 (e.g., by performing downconversion, baseband processing, and/or further conditioning).

With further reference to FIG. 5, and also referencing FIG. 2, display device 310 may be used to display or otherwise provide the sensor data (or analyte data) or data derived therefrom to a user, server system 334, and/or partner device 315. Partner device 315 may utilize sensor data or a derivative data derived therefrom in the administration of medicaments (e.g., insulin) and/or diabetes management guidance to the user. As used herein, the terms "radio unit," "receiver," "transmitter," and/or "transceiver" may in some cases be referenced and generally may refer to a device that can wirelessly transmit and/or receive data. Analyte sensor system 308 may further include storage 515 (e.g., which may be part of item 12 in FIG. 1) and real time clock (RTC) 540 (e.g., which may be part of item 12 in FIG. 1), for storing and tracking sensor and other data.

Analyte sensor system 308 may also include activation detection circuit 520. Activation detection circuit 520 may optionally operate in conjunction with activation detection component 545. Activation detection component 545 may be integral to analyte sensor system 308, may be a component attachable thereto, and/or may be external thereto. Examples of activation detection circuit 520 and/or activation detection component 545 may include radio unit 510 and/or antenna circuitry for communication of wireless information, e.g., via BLE, NFC, RFID, and/or any other wireless technique or format. For instance, activation detection circuit 520 and/or activation detection component 545 may in certain embodiments use, include, and/or involve antenna 506 and/or antenna 512. For example, analyte sensor system 308 may transition into an operational state in response to a modified signal received using antenna 512, where the modified signal is generated using an input signal received using antenna 506. In embodiments, the received signal may come from display device 310. By way of further example, analyte sensor system 308 may obtain pairing information from the modified signal received using antenna 512, where the modified signal is generated using an input signal received using antenna 506. In some embodiments, the modified signal may be a wakeup command signal, or the like, sent via NFC and/or other electronic signals by the display device. By way of additional example, analyte sensor system 308 may exchange analyte information or other control signaling—including for example control signaling that may be related to the exchange of analyte or other information, may be related to power management, and/or may be related to other features of the present disclosure (e.g., interfacing with partner device(s) 315)—from the modified signal received using antenna 512, where the modified signal is generated using an input signal received using antenna 506. In any of the above examples, the input signal may be transmitted to antenna 506 from, for example, a remote device/source such as display device 310, partner device 315, and/or server system 334, or the like (e.g., using an NFC, BLE, and/or other protocol, and/or using any other kind of wireless transmission).

Analyte sensor system 308 in example implementations gathers analyte data using sensor 530 and transmits the same or a derivative thereof to display device 310, partner device 315, and/or server system 334. Data points regarding analyte values may be gathered and transmitted over the life of sensor 530. New measurements and/or related information may be transmitted often enough for a remote device/individual to adequately monitor analyte (e.g., glucose) levels.

It is to be appreciated that some details of the processing, gathering, and exchanging data by analyte sensor system 308, partner devices 315, and/or display device 310 etc. are provided elsewhere herein. It will be appreciated upon studying the present disclosure that analyte sensor system 308 may contain several like components that are described with respect to FIGS. 1, 2, 3A, 3B, and/or 4, at least for some embodiments herein. The details and uses of such like components may therefore be understood vis-à-vis analyte sensor system 308 even if not expressly described here with reference to FIG. 5.

In embodiments, a wireless/antenna-based technique may be used for purposes of activating analyte sensor system 308. For example, activation detection component 545, portions of which may be internal to analyte sensor system 308 and/or portions of which may be external to analyte sensor system 308, may include a component such as an NFC or RFID tag that may be placed in proximity to analyte sensor system 308. By way of example, such a tag may be located within an applicator for analyte sensor system 308 or within packaging for analyte sensor system 308 (see, e.g., FIGS. 6A and 6B). Analyte sensor system 308 may, at a regular interval, interrogate the tag to establish a proximity relationship. For example, analyte sensor system 308 may use a transmitter that may be part of the radio unit 510 to send/receive a ping or other message/signal to/from the tag. If analyte sensor system 308 does not receive a response to the ping or other message/signal, the lack of response may be used to indicate deployment of analyte sensor system 308 (e.g., insertion of analyte sensor 530) and therefor trigger exiting a lower power mode. In embodiments where analyte sensor system 308 continues to send ping messages after deployment, analyte sensor system 308 can receive input indicating that deployment has occurred (e.g., via a GUI of a connected display device 310), and as a result cease sending the ping messages. In some cases, the tag may be an active component that pings analyte sensor system 308 or the activation detection component. In such cases, if analyte sensor system 308 stops receiving pings from the tag, the lack of ping messages being received may be used to indicate deployment of analyte sensor system 308.

In example embodiments, during deployment of analyte sensor system 308 or removal of the same from packaging, wireless signaling (e.g., BLE, NFC, WiFi, cellular, RFID, and/or any type of wireless signaling) may be used to detect an alteration in the proximity relationship between analyte sensor system 308 and a reference point such as the packaging, and the alteration may be used to trigger analyte sensor system 308 to exit a lower power state. Alterations of the proximity relationship may also be detected using measurements that may be made, for example, using radio unit 510, such as RSSI or other channel measurements that may indicate proximity from a reference point. These measurements (e.g., RSSI) may be used to trigger analyte sensor system 308 to exit the lower power state when the estimated distance between the reference location and analyte sensor system 308 satisfies a condition such as specific threshold distance for example. Additionally, in certain embodiments, NFC or other wireless signaling can be used to provide a wakeup command (e.g., from one or more display devices) to analyte sensor system 308 to activate or change the operational state of analyte sensor system 308. In embodiments, the wireless signaling may be boosted using the booster antenna, as described above. Alternatively, the lack of an NFC ping, or the NFC ping dropping below a certain power level, can be used to indicate a lack of proximity and hence trigger activation of analyte sensor system 308.

In other examples, analyte sensor system 308 may utilize a radio frequency echo to trigger analyte sensor system 308 to exit a lower power state. For example, analyte sensor system 308 may use radio unit 510 to intermittently emit an RF signal and monitor the echo of the same for parameters that may be known (e.g., well characterized) for a given environment (e.g., within packaging or an applicator). Such parameters may include signal strength, Doppler, distance, density, and material, by way of example. If subsequent emissions and resulting echoes change, this may indicate a change in environment that may be used to trigger activation. Accordingly, embodiments involve detecting environmental changes using radio waves to determine range, angle, or velocity of objects surrounding analyte sensor system 308 using bounce-back of transmitted signals to characterize (e.g., changes) in the surrounding environment. For example, phase angle and the like can be measured to characterize the surrounding environment. As such, analyte sensor system 308 may then transition to an active or operational mode from the lower-power mode.

Figure 6A:
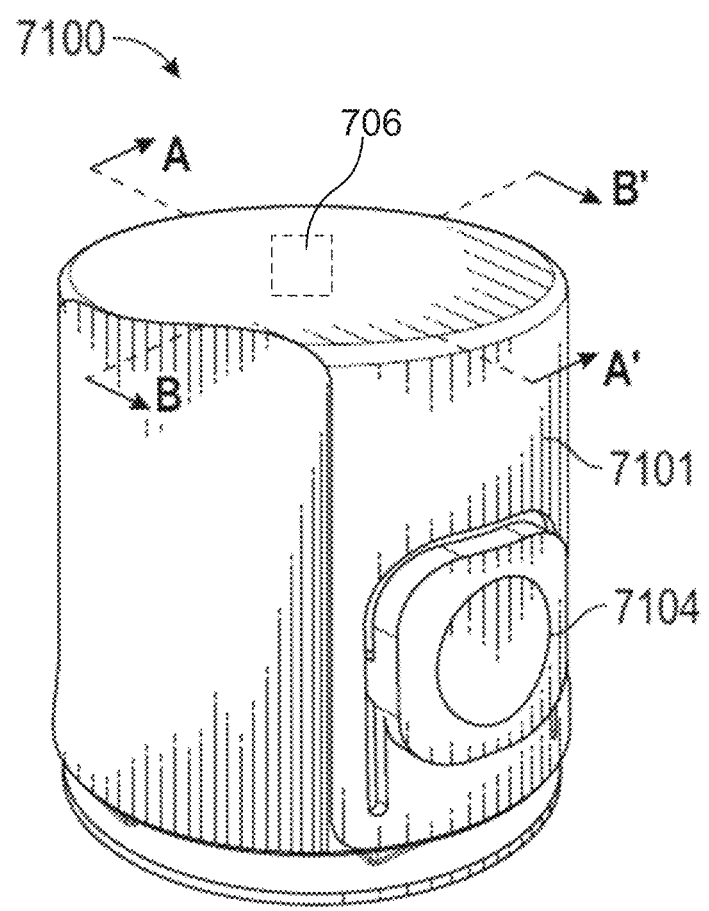
FIG. 6A illustrates aspects of an example application apparatus according to embodiments of the present disclosure.

FIG. 6A illustrates applicator 7100 for an on-skin sensor assembly of analyte sensor system 308 (e.g., on-skin assembly 360 described in connection with FIGS. 3A, 3B, and 4), according to embodiments of the disclosure. Applicator 7100 may include activation element 7104 disposed on a side of applicator 7100, for example, on a side of outer housing 7101 of applicator 7100. In some embodiments, activation element 7104 may be a button, a switch, a toggle, a slide, a trigger, a knob, a rotating member, a portion of applicator 7100 that deforms and/or flexes, or any other suitable mechanism for activating an insertion of analyte sensor 530 and/or retraction assembly of applicator 7100. In some embodiments, activation element 7104 may be disposed in any location, e.g., a top, upper side, lower side, or any other location of applicator 7100. Applicator 7100 may be large enough for a host to grasp with a hand and push, or otherwise activate, activation element 7104 with, for example, a thumb, or with an index finger and/or a middle finger. Applicator 7100 may be sized appropriately to house analyte sensor system 308, as well as one or more components of activation detection component 545 described above.

Also shown in FIG. 6A is antenna 706. In embodiments, aspects of antenna 706 may be substantially similar to antenna 506 discussed above in connection with FIG. 5. In embodiments, antenna 706 may be mechanically coupled to applicator 7100, including, for example, to any combination of an outside, inside, or other portion of applicator 7100. Applicator 7100 may be configured with one or more safety features such that applicator 7100 can be prevented from activating until the safety feature is deactivated. In one example, the one or more safety features may prevent applicator 7100 from activating unless applicator 7100 is pressed against the skin of a host with sufficient force. Moreover, applicator 7100 may be further configured such that one or more components therein retract based at least in part on the one or more components pushing against the skin of the host with a force exceeding a predetermined threshold, rather than based on the one or more components translating beyond a predetermined and static distal position. In other words, applicator 7100 may implement force-based retraction triggering rather than being limited to displacement-based retraction triggering.

Figure 6B:
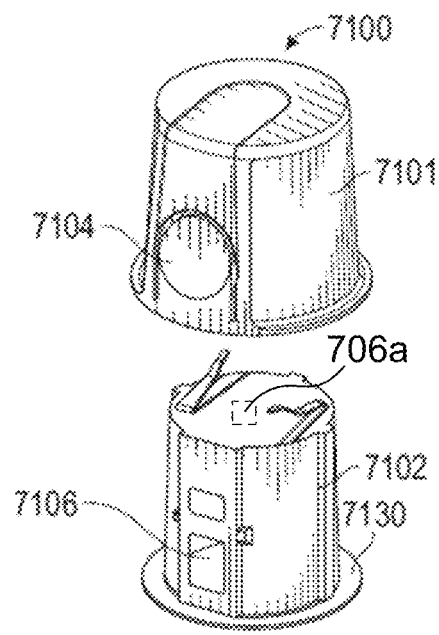
FIG. 6B illustrates another view of an example application apparatus according to embodiments of the present disclosure.
Figure 6B:
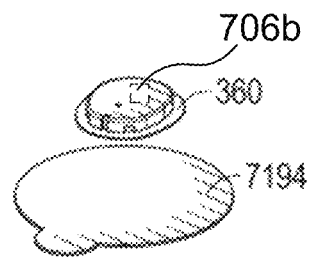

FIG. 6B illustrates an exploded perspective view of applicator 7100 of FIG. 6A, according to some embodiments. As shown, applicator 7100 may include outer applicator housing 7101 that may include activation element 7104. Outer applicator housing 7101 may be configured to translate in a distal direction by a force applied by a host to applicator 7100, specifically to inner housing 7102, thereby aligning activation element 7104 in a position that allows applicator 7100 to fire.

Applicator 7100 can optionally include inner housing 7102, configured to house at least one or more mechanisms utilized to apply analyte sensor assembly 360 (for example, as referenced above in connection with FIG. 3A) to the skin of a host. As mentioned above, analyte sensor assembly 360 may include or house analyte sensor system 308. A distal surface 7130 of a bottom opening of inner housing 7102 may define a bottom surface of applicator 7100. In some embodiments, upon applicator 7100 being pressed against the skin of a host, the skin may deform in a substantially convex shape at distal surface 7130 such that at least a portion of a surface of the skin is disposed at the bottom opening of applicator housing 7102 extends into the bottom opening of inner housing 7102 beyond a plane defined by distal surface 7130 in a proximal direction. One or more components of activation detection component 545 described above may be included in or on inner housing 7102, such as, for example, NFC components, magnets, etc., or any other of the components describe above that may be external to analyte sensor system 308. In some embodiments, barrier layer 7194 may be disposed over the bottom opening of inner housing 7102.

FIG. 6B also shows antenna 706a. In embodiments, aspects of antenna 706a may be substantially similar to antenna 706 discussed above in connection with FIG. 6A. In embodiments, antenna 706a may be mechanically coupled to outer housing 7101 and/or inner housing 7102 of applicator 7100. For example, antenna 706a may be integrated into outer housing 7101 and/or inner housing 7102. Alternatively or additionally, antenna 706a may be otherwise affixed (e.g., adhered, bonded, friction fit, clipped, soldered, screwed, or the like) to outer housing 7101 and/or inner housing 7102 (e.g., to an inner or outer surface or another portion thereof). In embodiments, antenna 706a may be mounted on and/or to a PCB, substrate(s), and/or other components that may be located on and/or within applicator 7100 or otherwise mechanically coupled thereto. In embodiments, antenna 706a may be a passive antenna, as described above, that may not be coupled to any electronic components.

In embodiments, at least a portion of antenna 706a is internal to applicator 7100. For example, relative to outer housing 7101 and/or inner housing 7102 of applicator 7100, at least a portion of antenna 706a may be internal to applicator 7100. In such examples, the portion(s) of antenna 706a that are located within applicator 7100 may be radiating portions of antenna 706a or other portions thereof (e.g., feeding portions, mounting portions, etc.). Additionally or alternatively, as alluded to above, in embodiments, at least a portion of antenna 706a is external to applicator 7100. For example, relative to outer housing 7101 of applicator 7100, at least a portion of antenna 706a may be external to applicator 7100. In such examples, the portion(s) of antenna 706a that are located external to applicator 7100 may be radiating portions of antenna 706a or other portions thereof (e.g., feeding portions, mounting portions, etc.). Additionally or alternatively, in embodiments, at least a portion of antenna 706a resides within one or more of outer housing 7101 and inner housing 7102 of applicator 7100. For example, at least a portion of antenna 706a may be encased or otherwise contained or integrated within a portion one or more of outer housing 7101 and inner housing 7102 of applicator 7100. In such examples, the portion(s) of antenna 706a that may be within outer housing 7101 and/or inner housing 7102 may be radiating portions of antenna 706a or other portions thereof (e.g., feeding portions, mounting portions, etc.). Additionally or alternatively, in embodiments, at least a portion of antenna 706a resides between outer housing 7101 and inner housing 7102.

It should be appreciated that although outer housing 7101 and inner housing 7102 are referenced above, there may be multiple pieces or components of the housing(s), or other structural components, for applicator 7100, and portion(s) of antenna 706a may be located in any number of such pieces or components, including being distributed through any number of such pieces or components. In some cases, the above-described examples involve antenna 706a being located relative to another housing or structural component of applicator 7100. For example, there may be one or more other housings and/or one or more structural components for applicator 7100, and portion(s) of antenna 706a may be located relative to one or more of such housings and/or structural components in the above-described fashion. Portion(s) of antenna 706a may also be distributed through any number of such housings or structural components for applicator 7100. It should also be appreciated that where antenna 706 or antenna 706a is mechanically coupled or otherwise affixed to applicator 7100, antenna 706 or antenna 706a is typically used for exchanging pairing and/or activation related signaling before deployment of analyte sensor system 308.

FIG. 6B also shows antenna 706b that may be mechanically coupled or otherwise affixed to on-skin assembly 360. In embodiments, aspects of antenna 706b may be substantially similar to antenna 306, antenna 406, and/or antenna 506 discussed above in connection with FIGS. 3A, 3B, 4, and 5.

Activation of applicator 7100 may include a host pressing applicator 7100 against the skin with sufficient force to translate outer housing 7101 in a distal direction toward and with respect to inner housing 7102 until activation element 7104 is aligned with aperture 7106 of inner housing 7102. Once such an alignment is achieved, a host may initiate (e.g., pushing) activation element 7104. In some other embodiments, applicator 7100 may be configured such that activation element 7104 may be activated first, but that actual insertion is not triggered until outer housing 7101 is translated sufficiently in the distal direction toward and with respect to inner housing 7102. In yet other embodiments, activation element 7104 may be biased toward a center of applicator 7100 such that activation element 7104 need not be explicitly activated by the host but, instead, activation element 7104 may be configured to automatically initiate insertion upon outer housing 7101 being translated sufficiently in the distal direction toward and with respect to inner housing 7102.

In certain embodiments, activation detection circuit 520 and/or activation detection component 545 may include additional components that may be added internally to and/or externally from analyte sensor system 308 specifically for creating detectable events that may be used to trigger activation of analyte sensor system 308 without user intervention.

Activation detection component 545 may include induction coils or may include antenna 506, for example on the perimeter of analyte sensor system 308, that may be used to generate current (e.g., or other electrical signal) via electromagnetic response. The motion of the applicator withdrawing the needle, rod, or other magnetic element can create relative motion between the same and the coil/antenna of analyte sensor system 308. This current or other electrical signal can then be used to trigger activation of analyte sensor system 308. In some cases analyte sensor system 308 may already include antenna 506, and thus this feature may not require the addition of components to analyte sensor system 308.

In embodiments, the detection element may use or include one or more of antenna 506 and antenna 512. For example, the detection element may use or involve an input or other wireless signal, such as an NFC, BLE, cellular, WiFi, or any other wireless signal. For example, antenna 512 that may be within or electrically coupled to analyte sensor system 308 or one or more components thereof may be used to receive such a signal from a source external to analyte sensor system 308 (e.g., display device 310) to trigger activation. For example, antenna 512 (e.g., which may in some cases be or include an NFC coil) can be placed in analyte sensor system 308 or on a skin adhesive patch and electrically coupled to analyte sensor system 308 or one or more components thereof. As mentioned above, in some cases, NFC or other wireless range or other characteristics may not be sufficient to effectively reach antenna 512 of analyte sensor system 308, for example when analyte sensor system 308 is inside an applicator. In such cases, antenna 506, which may in certain instances be a sympathetic antenna or the like, can be added, for example, to the outside of the applicator or in another location as described herein, to boost a signal from the external source/device to enable antenna 512 to better receive the signaling from the external source/device. As mentioned above, antenna 506 may include one or more passive components but may also be, include, and/or use one or more active components for additional signal boosting. In embodiments, NFC or other wirelessly induced wake up can cause rapid, immediate, and/or forced communication between analyte sensor system 308 and a smartphone, a wearable electronic device, or any other electronic device. As described above, antennas 506 and 512 can also be used to facilitate the wireless exchange of pairing information, analyte information, and/or other signaling such as control signaling.

It should be appreciated that each of the above-described techniques can be used alone or in combination with any of the other above-described techniques for purposes of causing analyte sensor system 308 to exit a lower power state. The technique(s) employed may depend upon system design considerations, for example, including considerations regarding power consumption, weight, size, and level of user interactivity, among other considerations. It should also be appreciated that the above-described features and techniques may not be limited to preconnected systems but may in certain embodiments be implemented using other systems (e.g., where such systems are non-preconnected).

D. Additional Aspects of Embodiments

One of skill in the art will appreciate upon studying the present disclosure that various additional embodiments and/or aspects of certain embodiments, that may not described explicitly herein, are within the spirit and scope of the present disclosure.

Figure 7:
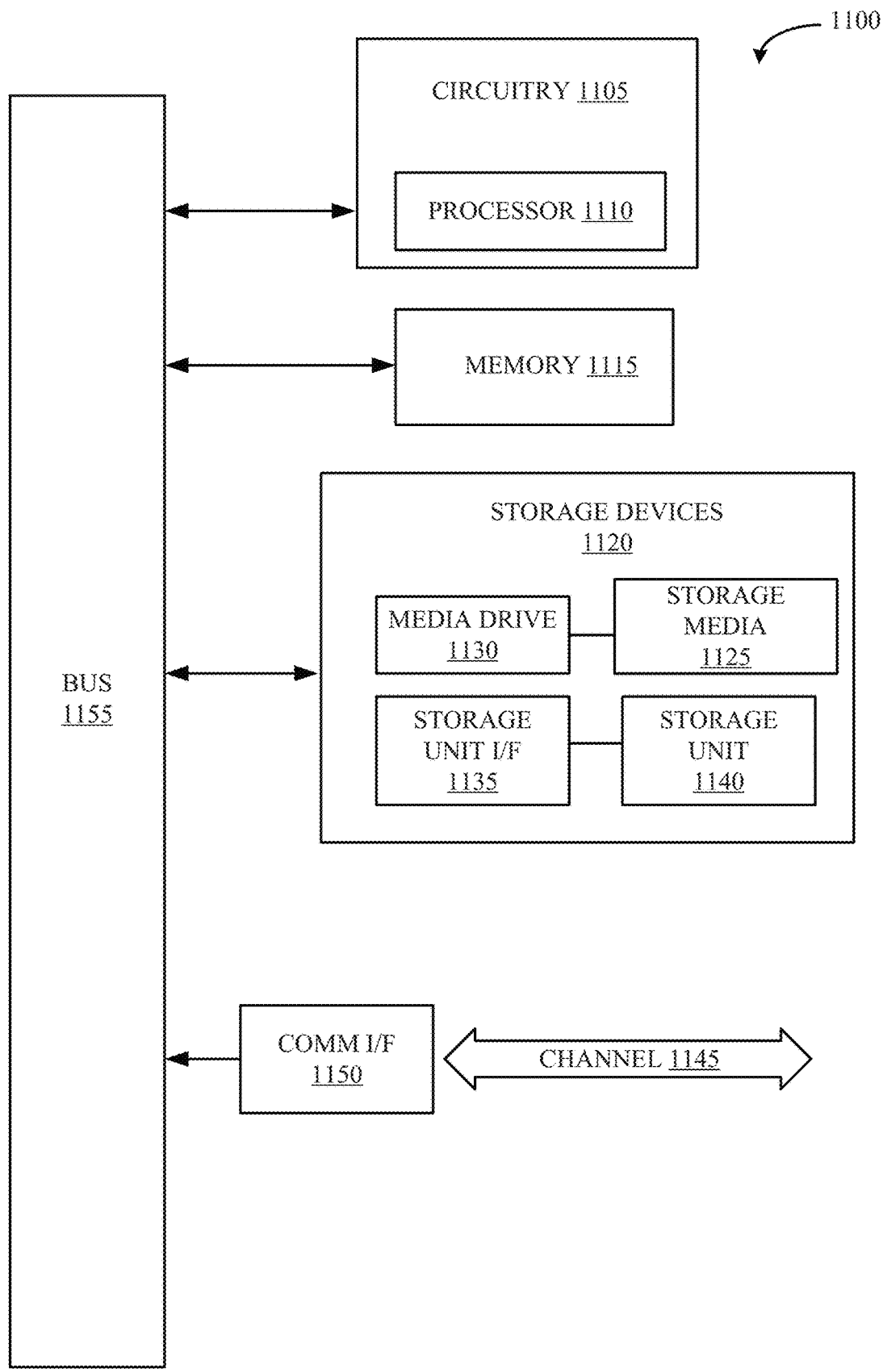
FIG. 7 illustrates an example computing module in accordance with embodiments of the present disclosure.

FIG. 7 illustrates example computing module 1100, which may in some instances include a processor/microprocessor/controller resident on a computer system (e.g., in connection with server system 334, any of the display devices described herein (e.g., display devices 120, 130, 140, 310(*a, b*, etc.), partner devices 315(*a, b*, etc.), and/or analyte sensor system 8, 308, etc. Computing module 1100 may be used to implement various features and/or functionality of embodiments of the systems, devices, apparatuses, and methods disclosed herein. With regard to the above-described embodiments set forth herein in the context of systems, devices, apparatuses, and methods described with reference to the various FIGS. of the present disclosure, including embodiments of analyte sensor system 308, display device 310, partner devices 315, server system 334, and components of or used in connection with the foregoing as described and/or contemplated herein, etc., one of skill in the art will appreciate upon studying the present disclosure the additional variations and details regarding the functionality of these embodiments that may be carried out by computing module 1100. In this connection, it will also be appreciated by one of skill in the art upon studying the present disclosure that features and aspects of the various embodiments (e.g., systems, devices, and/or apparatuses, and the like) described herein may be implemented with respected to other embodiments (e.g., methods, processes, and/or operations, and the like) described herein without departing from the scope or spirit of the disclosure.

As used herein, the term module may describe a given unit of functionality that may be performed in accordance with one or more embodiments of the present application. As used herein, a module may be implemented utilizing any form of hardware, software, or a combination thereof. For example, one or more processors, controllers, ASICs, PLAs, PALs, CPLDs, FPGAs, logical components, software routines or other mechanisms may be implemented to make up a module. In example implementations, the various modules described herein may be implemented as discrete modules or the functions and features described may be shared in part or in total among one or more modules. In other words, as would be apparent to one of ordinary skill in the art after reading this description, the various features and functionality described herein may be implemented in any given application and may be implemented in one or more separate or shared modules in various combinations and permutations. Even though various features or elements of functionality may be individually described or claimed as separate modules, one of ordinary skill in the art will understand that these features and functionality may be shared among one or more common software and hardware elements, and such description shall not require or imply that separate hardware or software components are used to implement such features or functionality.

Where components or modules of the application are implemented in whole or in part using software, in one embodiment, these software elements may be implemented to operate with a computing or processing module capable of carrying out the functionality described with respect thereto. One such example computing module is shown in FIG. 7. Various embodiments are described in terms of example computing module 1100. After reading this description, it will become apparent to a person skilled in the relevant art how to implement the application using other computing modules or architectures.

Referring now to FIG. 7, computing module 1100 may represent, for example, computing or processing capabilities found within mainframes, supercomputers, workstations or servers; desktop, laptop, notebook, or tablet computers; hand-held computing devices (tablets, PDA's, smartphones, cell phones, palmtops, etc.); other display devices, application-specific devices, or other electronic devices, and the like, depending on the application and/or environment for which computing module 1100 is specifically purposed.

Computing module 1100 may include, for example, one or more processors, microprocessors, controllers, control modules, or other processing devices, such as a processor 1110, and such as may be included in circuitry 1105. Processor 1110 may be implemented using a special-purpose processing engine such as, for example, a microprocessor, controller, or other control logic. In the illustrated example, processor 1110 is connected to bus 1155 by way of circuitry 1105, although any communication medium may be used to facilitate interaction with other components of computing module 1100 or to communicate externally.

Computing module 1100 may also include one or more memory modules, simply referred to herein as main memory 1115. For example, random access memory (RAM) or other dynamic memory may be used for storing information and instructions to be executed by processor 1110 or circuitry 1105. Main memory 1115 may also be used for storing temporary variables or other intermediate information during execution of instructions to be executed by processor 1110 or circuitry 1105. Computing module 1100 may likewise include a read only memory (ROM) or other static storage device coupled to bus 1155 for storing static information and instructions for processor 1110 or circuitry 1105.

Computing module 1100 may also include one or more various forms of information storage devices 1120, which may include, for example, media drive 1130 and storage unit interface 1135. Media drive 1130 may include a drive or other mechanism to support fixed or removable storage media 1125. For example, a hard disk drive, a floppy disk drive, a magnetic tape drive, an optical disk drive, a CD or DVD drive (R or RW), or other removable or fixed media drive may be provided. Accordingly, removable storage media 1125 may include, for example, a hard disk, a floppy disk, magnetic tape, cartridge, optical disk, a CD or DVD, or other fixed or removable medium that is read by, written to or accessed by media drive 1130. As these examples illustrate, removable storage media 1125 may include a computer usable storage medium having stored therein computer software or data.

In alternative embodiments, information storage devices 1120 may include other similar instrumentalities for allowing computer programs or other instructions or data to be loaded into computing module 1100. Such instrumentalities may include, for example, fixed or removable storage unit 1140 and storage unit interface 1135. Examples of such removable storage units 1140 and storage unit interfaces 1135 may include a program cartridge and cartridge interface, a removable memory (for example, a flash memory or other removable memory module) and memory slot, a PCMCIA slot and card, and other fixed or removable storage units 1140 and storage unit interfaces 1135 that allow software and data to be transferred from removable storage unit 1140 to computing module 1100.

Computing module 1100 may also include a communications interface 1150. Communications interface 1150 may be used to allow software and data to be transferred between computing module 1100 and external devices. Examples of communications interface 1150 include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface configured to operation with the communication media described herein. Software and data transferred via communications interface 1150 may in examples be carried on signals, which may be electronic, electromagnetic (which includes optical) or other signals capable of being exchanged by a given communications interface 1150. These signals may be provided to/from communications interface 1150 via channel 1145. Channel 1145 may carry signals and may be implemented using a wired or wireless communication medium. Some non-limiting examples of channel 1145 include a phone line, a cellular or other radio link, an RF link, an optical link, a network interface, a local or wide area network, and other wired or wireless communications channels.

In this document, the terms "computer program medium" and "computer usable medium" and "computer readable medium", as well as variations thereof, are used to generally refer to transitory or non-transitory media such as, for example, main memory 1115, storage unit interface 1135, removable storage media 1125, and/or channel 1145. These and other various forms of computer program media or computer usable/readable media may be involved in carrying one or more sequences of one or more instructions to a processing device for execution. Such instructions embodied on the medium, may generally be referred to as "computer program code" or a "computer program product" or "instructions" (which may be grouped in the form of computer programs or other groupings). When executed, such instructions may enable the computing module 1100, circuitry related thereto, and/or a processor thereof or connected thereto to perform features or functions of the present disclosure as discussed herein (for example, in connection with methods described above and/or in the claims), including, for example, when the same is/are incorporated into a system, apparatus, device and/or the like.

Various embodiments have been described with reference to specific example features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense.

Although described above in terms of various example embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; the term "set" should be read to include one or more objects of the type included in the set; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Similarly, the plural may in some cases be recognized as applicable to the singular and vice versa. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic, circuitry, or other components, may be combined in a single package or separately maintained and may further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration. Moreover, the operations and sub-operations of various methods described herein are not necessarily limited to the order described or shown in the figures, and one of skill in the art will appreciate, upon studying the present disclosure, variations of the order of the operations described herein that are within the spirit and scope of the disclosure.

In addition, the operations and sub-operations of methods described herein may be carried out or implemented, in some cases, by one or more of the components, elements, devices, modules, circuitry, processors, etc. of systems, apparatuses, devices, environments, and/or computing modules described herein and referenced in various of FIGS. of the present disclosure, as well as one or more sub-components, elements, devices, modules, processors, circuitry, and the like depicted therein and/or described with respect thereto. In such instances, the description of the methods or aspects thereof may refer to a corresponding component, element, etc., but regardless of whether an explicit reference is made, one of skill in the art will recognize upon studying the present disclosure when the corresponding component, element, etc. may be used. Further, it will be appreciated that such references do not necessarily limit the described methods to the particular component, element, etc. referred to. Thus, it will be appreciated by one of skill in the art that aspects and features described above in connection with (sub-) components, elements, devices, modules, and circuitry, etc., including variations thereof, may be applied to the various operations described in connection with methods described herein, and vice versa, without departing from the scope of the present disclosure.

What is claimed is:

1. A system for wireless communication of analyte information, the system comprising:
    an analyte sensor system, comprising:
        an analyte sensor adapted to gather information related to a level of an analyte in a host;
        analyte sensor electronics circuitry adapted to transmit and receive wireless signals using a first antenna, wherein the analyte sensor is electrically and mechanically coupled to the analyte sensor electronics circuitry before the analyte sensor is implanted into the host; and
        a second antenna adapted to receive an input signal from a source external to the analyte sensor system, and further adapted to wirelessly transmit a modified version of the input signal, wherein the second antenna is external to the analyte sensor electronics circuitry, and wherein the modified version of the input signal is one or more of a beam steered, phase adjusted, shaped, filtered, or conditioned version of the input signal, and
        wherein the analyte sensor electronics circuitry is further adapted to use the first antenna to wirelessly receive the modified version of the input signal, and wherein the analyte sensor system is further adapted to transition into an operational state in response to the modified version of the input signal received using the first antenna.

2. The system of claim 1, wherein the second antenna is mechanically coupled to an applicator or packaging for the analyte sensor system.

3. The system of claim 1, wherein the second antenna is mechanically coupled to the analyte sensor system.

4. The system of claim 3, wherein the second antenna is mechanically coupled to a housing of the analyte sensor system.

5. The system of claim 3, wherein the first antenna is different from the second antenna.

6. The system of claim 3, wherein at least a portion of the second antenna is external to the analyte sensor system relative to a housing of the analyte sensor system.

7. The system of claim 3, wherein at least a portion of the second antenna resides within a housing of the analyte sensor system.

8. The system of claim 1, wherein the modified version of the input signal received using the first antenna comprises pairing information transmitted to the analyte sensor system for purposes of connection establishment.

9. The system of claim 1, wherein the modified version of the input signal received using the first antenna comprises information transmitted to the analyte sensor system for purposes of exchanging the information related to the level of the analyte in the host.

10. A method of wireless communication using an analyte sensor system, the analyte sensor system comprising an analyte sensor and analyte sensor electronics circuitry, wherein the analyte sensor is adapted to gather information related to a level of an analyte in a host, wherein the analyte sensor is mechanically and electronically coupled to the analyte sensor electronics circuitry before the analyte sensor is implanted into the host, wherein the analyte sensor electronics circuitry is adapted to transmit and receive wireless signals using a first antenna, the method comprising:
    a second antenna wirelessly receiving an input signal from a source external to the analyte sensor system, wherein the second antenna is external to the analyte sensor electronics circuitry;
    generating a modified version of the input signal received from the source, the generating comprising one or more of beam steering, adjusting a phase, shaping, filtering, or conditioning the input signal;
    the second antenna wirelessly transmitting the modified version of the input signal to the analyte sensor system; and
    the analyte sensor electronics circuitry using the first antenna to receive the modified version of the input signal transmitted by the second antenna.

11. The method of claim 10, further comprising the analyte sensor system transitioning into an operational state in response to the modified version of the input signal received using the first antenna.

* * * * *